(12) United States Patent
Strobel et al.

(10) Patent No.: US 7,387,888 B2
(45) Date of Patent: Jun. 17, 2008

(54) CORONAMYCINS

(75) Inventors: Gary A. Strobel, Bozeman, MT (US); Debbie S. Yaver, Davis, CA (US); Uvidelio F. Castillo, Bozeman, MT (US); David Ezra, Adanim (IL)

(73) Assignees: Montana State University, Bozeman, MT (US); Novozymes Biotech Inc., Davis, CA (US)

( * ) Notice: Subject to any disclaimer, the term of this patent is extended or adjusted under 35 U.S.C. 154(b) by 233 days.

(21) Appl. No.: 11/064,486

(22) Filed: Feb. 24, 2005

(65) Prior Publication Data

US 2005/0260182 A1    Nov. 24, 2005

Related U.S. Application Data

(60) Provisional application No. 60/546,964, filed on Feb. 24, 2004.

(51) Int. Cl.
*C12C 1/00*      (2006.01)

(52) U.S. Cl. ...................................................... 435/93

(58) Field of Classification Search .................. 435/93
See application file for complete search history.

(56) References Cited

OTHER PUBLICATIONS

Strobel et al , Natural Products from Endophytic Microorganisms, Journal of Natural Products, vol. 67, p. 257-268, Feb. 2004.*

* cited by examiner

*Primary Examiner*—Ruth A Davis
*Assistant Examiner*—Tiffany M Gough
(74) *Attorney, Agent, or Firm*—Klarquist Sparkman, LLP

(57) ABSTRACT

The present invention relates to isolated strains of a *Streptomyces* spp. which are endophytes of dicotyledonous plants and to methods for selecting such strains. The present invention also relates to a biologically active compound called coronamycin obtained from endophytic Streptomycetes isolated from higher plants. The present invention further relates to compositions of such compounds and to methods of protecting plants against attack by a plant pathogen and methods of inhibiting bacterial growth, fungal growth, viral infection, growth of parasitic organisms, and cancer cell growth with such compositions.

8 Claims, 4 Drawing Sheets

FIGURES
UPPER LEFT BAR = 10PM
UPPER RIGHT BAR = 10PM
LOWER LEFT BAR = 10PM
CENTER RIGHT BAR = 10PM
LOWER RIGHT BAR = 10PM

CORONAMYCINS

CROSS REFERENCES TO RELATED APPLICATIONS

This application claims priority to Provisional Application 60/546,964, filed Feb. 24, 2004, which is hereby specifically incorporated by reference in its entirety.

STATEMENT OF RIGHTS TO INVENTIONS MADE UNDER FEDERALLY SPONSORED RESEARCH

This invention was partially made with government support under Vaadia-BARD post doctoral award No. FI-321-2001 from the United States-Israel Binational Agricultural Research and Development Fund and with funds from the United States National Science Foundation, grant No. 0244206. The U.S. Government has certain rights in this invention.

BACKGROUND OF THE INVENTION

1. Field of the Invention

The present invention relates to biologically active compounds called coronamycins obtained from endophytic Streptomycetes isolated from higher plants. The present invention also relates to compositions comprising the coronamycin as well as methods of using the compositions.

2. Description of the Related Art

The bacterial order Actinomycetales includes several genera of bacteria similar to fungi in that they have a branching, filamentous structure. The branching filaments of the Actinomycetes eventually develop a network of strands called mycelium, which are similar in appearance to the mycelium of some fungi. Actinomycetes also form spores.

Actinomycetes are particularly valued for the property of producing antibiotics, with the most productive genus in this group being *Streptomyces*. Over 50 commercially important antibiotics have been isolated from *Streptomyces* spp., including streptomycin, neomycin, chloramphenicol and tetracyclines. Streptomycetes are found worldwide, and are a particularly significant as members of the soil microflora. Streptomycetes are also metabolically diverse, however, and are found in a great variety of ecological environments.

Actinomycetes, in general, are not reported to be endophytes on higher plants, though recently a *Streptomyces* sp. was reported on an annual plant—*Lolium perenne* (Guerny and Mantle, 1993, *J. Nat. Prod.* 56: 1194-1198). This lolium endophyte produces a weak antibiotic designated as methylalbonoursin, which is a diketopiperazine, condensed from leucine and phenylalanine. Streptomycetes which are used as a source of biologically active compounds, such as antibiotics, have all been isolated from soil.

The development of drug resistance in human pathogenic bacteria, such as *Staphylococcus, Mycobacterium, Streptococcus, Enterococcus* and others, places an ever increasing importance on the search for new antibiotics, as diseases caused by such bacteria represent a clear and growing threat to world health (NIH, 2001, NIAID Global Health Research Plan for HIV/AIDS, Malaria and Tuberculosis. U.S. Department of Health and Human Services. Bethesda, Md.). For instance, tuberculosis is the second leading cause of death in the world, killing approximately 2.5 million people per year. Up to 30% of the world's peoples are carriers of this pathogen (NIH, 2001, supra). The incidence of tuberculosis is rising in the world's population, in part due to the increased incidence of patients with HIV/AIDS, but also due to the development of drug resistance in strains of *M. tuberculosis* (Raviglione et al., 1995, *J. Amer. Med. Assoc.* 273, 220-226.; Pablosmendez et al., 1997, *New England J. Med.* 338, 1641-1649).

In addition to the problems of drug resistance in pathogenic bacteria there is also a need for more and better antimycotics, as the human population is developing more fungal infections. This is particularly an issue with HIV/AIDS patients, but also a concern with patients with organ-transplants, who must take immunosuppressive drugs to maintain continuity of the transplanted organ. In both cases, patients with these difficulties have immune systems that are weakened. Antifungal agents that are currently available, such as amphotericin B, are toxic, and often ineffective (Walsh, 1992, In "Emerging Targets in Antibacterial and Antifungal Chemotherapy" pp. 349-373. Ed. J. A. Sutcliffe and N. H. Georgopapadakou. London: Chapman and Hall; Walsh and Finberg, 1999, *New England J. Med.* 340, 764-771).

The increased incidence of parasitic protozoan infections is a further cause of concern. The most important of these is malaria caused by *Plasmodium* spp. that kills up to 1.5-3 million people and produces up to nearly 500 million cases per year (NIH, 2001, supra). It is estimated that nearly 40% of the world's population is at risk of becoming infected with malaria. Global warming as well as "airport malaria" are factors contributing to the increasing spread of this disease. Another factor contributing to the increased threat of death caused by malaria is the development of drug resistance in the *Plasmodium* spp. populations (NIH, 2001, supra). In some cases, treatment of malaria and other infectious diseases has been possible with the availability of antibiotics originally derived from soil-born *Streptomyces* spp. (Waksman, 1967, The Actinomycetes. Ronald Press Co. New York.; Waksman and Lechevalier 1953, Actinomycetes and Their Antibiotics. Williams and Wilkins Co., Baltimore; and Arai, 1976, Actinomycetes: The Boundary Microorganisms. Toppan Co. Ltd, Singapore).

There is also a need for environmentally sound ways to grow the world's food, and new methods of controlling pests and pathogens are continuously needed in this field, as well (Overton et al., 1996, Ecologically Based Pest Mangement—New Solutions for a New Century. Natl. Aca. Press. Washington D.C.). In the past, the major source of pesticidal agents came from organic synthesis. Recently, interest has increased for using more environmentally friendly methods in agricultural production, including naturally-occurring biological compounds.

It is an object of the present invention to provide endophytic streptomycetes from higher plants, and extracts and compounds thereof, with biological activity.

SUMMARY OF THE INVENTION

The present invention relates to an isolated compound called coronamycin which has biological activity, which comprises a peptide chain comprising component 1, component 2, tyrosine, methionine, and leucine in molar ratios of 2:2:1:1:3, respectively; and has UV absorbances at 208, 214, and a broad band at 270 nm with millimolar extinction coefficients of 2.86, 2.03, and 0.23, respectively; HPLC retention time of 36.43 minutes on a Microsorb 100-5 C-18 column, 250×4.6 mm, using 20% acetonitrile:80% water for 90 minutes as an initial elution solvent programmed to a final concentration of 80% acetonitrile at a flow rate of 2 ml/minute; MS/MS component ions of 1203.4, 1217.9, 1185.8, 1199.8, and 1233.5 daltons; a $^1$H NMR spectrum of FIG. 4;. The present invention further relates to compositions of such a compound.

The present invention also relates to isolated strains of a *Streptomyces* spp. which is an endophyte of a dicotyledonous plant and has the identifying characteristics of *Streptomyces* sp NRRL 30701.

The present invention also relates to methods for selecting a strain of endophytic *Streptomyces* spp. having biological activity, comprising:

(a) culturing tissue from the interior region of a dicotyledonous plant on nutrient media for a time sufficient to permit colony formation by a strain of endophytic *Streptomyces* spp. associated with the tissue; and (b) selecting a *Streptomyces* sp. strain having biological activity similar to the biological activity of *Streptomyces* sp NRRL 30701.

The present invention also relates to methods of protecting plants against attack by a plant pathogen and methods of inhibiting bacterial growth, fungal growth, viral infection, growth of parasitic organisms, and cancer cell growth.

DETAILED DESCRIPTION OF THE INVENTION

Isolated Endophytic Microorganisms

Figure 1:
FIG. 1 shows a plant specimen of *Monstera* sp. growing on a trunk in the upper Amazon of Peru from which the endophytic *Streptomyces* sp. MSU-2110 (NRRL 30701) was isolated.

The present invention relates to isolated strains of a *Streptomyces* spp. which are endophytes of dicotyledonous plants. The endophytic *Streptomyces* spp. of the present invention produce biologically active substances called the coronamycins. The methods described herein allow the selection of, particularly, endophytic Streptomycetes by isolating strains, and purifying and characterizing the bioactive components of these microorganisms.

The term "endophytes" is defined herein as plant-associated microorganisms that live in the interstitial spaces of living plant tissues (Bacon and White, Microbial Endophytes. Marcel Dekker Inc., N.Y., 2000). Higher plants may host one or more endophytic microbes, which include fungi, bacteria, and actinomycetes. Endophytes reside in the tissues beneath the epidermal cell layers. It is well understood that endophytic infections are inconspicuous (Bacon and White, 2000, supra). As a result, the host tissues are transiently symptomless and colonization of the tissues is internal to the surface of the plant. The exact physical relationship of the endophyte to the plant remains obscure, because it is extremely difficult, for example, by electron microscopic techniques, to find an endophyte within plant tissues. The relationship that any given endophyte establishes with the plant likely varies from truly symbiotic to something bordering on pathogenic.

While the Actinomycetes, as a group, are the world's greatest biological source of antibiotics with over 2000 that have been reported (Waksman, The Actinomycetes. Ronald Press Co. New York, 1967; Arai, Actinomycetes: The Boundary Microorganisms. Toppan Co. Ltd, Singapore 1976), until recently none had ever been isolated that are endophytic on higher plants (see, Castillo et al., 2002, *Microbiology* 148: 2675-2685 and Castllo et al., 2003, *FEMS Mcrobiology Letters* 224:183-190). The single microbial genus that has contributed the greatest wealth of antibiotic substances to the world is *Streptomyces* spp. (Waksman, 1967, supra). The successful isolation of representatives of this important group of microorganisms, as endophytes of higher plants, provides an entirely new source of biologically active products.

In the present invention, the isolation of specific endophytic Streptomycetes that produce the coronamycins involves selecting one or more plants as a source of the endophyte. Usually this selection process is conducted on the basis of the environment, age, or natural history of a given plant. Such selection methods involve culturing tissue from the interior region of a dicotyledonous plant, e.g., trees, vines, and shrubs, on nutrient media for a time sufficient to permit colony formation by a strain of endophytic *Streptomyces* spp. associated with the plant tissue and selecting one or more *Streptomyces* sp. strains demonstrating the biological activity of interest. Various means can be used to select the endophytic *Streptomyces* spp. strains, and the strains can be tested through any of numerous methods known in the art to discover a biological activity of interest, either by measuring some activity of the strains directly, i.e., by zones of inhibition, or by preparing and testing extracts or purified compounds from the strains. The biological activity of interest can control or inhibit growth or proliferation of cells, such as cancer cells, or can possess an antibiotic property against a pathogenic organism, such as fungal pathogens, viral pathogens, bacterial pathogens, insect pathogens, or parasitic organisms.

In a preferred embodiment, the endophytic streptomycete is *Streptomyces* sp. NRRL 30701. *Streptomyces* sp. NRRL 30701 was recovered as isolate P-25-2-4 from a small epiphytic vine found in the Manu region of the upper Amazon of Peru. The vine is known locally in the Manu region as "follow-me vine" (*Monstera speciosa*). This organism was not isolated from any of a number of other trees and vines growing in the Lake Sandoval region of the upper Amazonian basin, including *Heliconia* sp., *Piper* sp., *Philodendron* sp., *Ochroma pyramidale*, and *Caryota urens*.

*Streptomyces* sp. produces a set of novel compounds, designated the coronamycins, which contribute no coloration to cultures.

Figure 2:
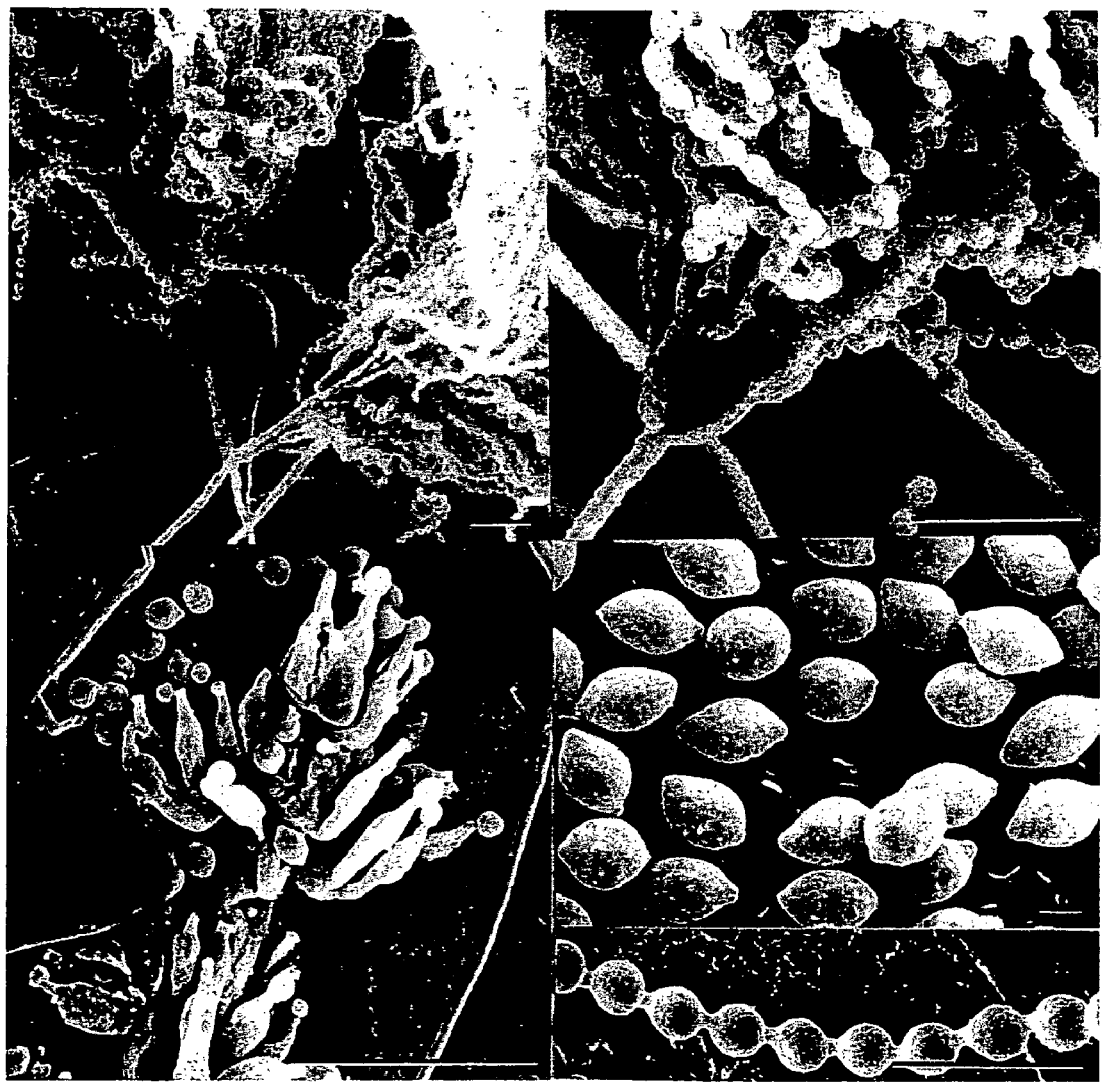
FIG. 2 shows scanning electron micrographs of (a) fruiting structures, (b) obpyriform verticils arranged in a whorl, (c) verticils without spores, (d) lemon-shaped individual spores, and (e) a chain of spores. All bars equal 10 microns except (d) which equals 1 micron.

When transferred and grown on PDA, the isolate P-25-2-4 produced a whitish fluffy mycelial growth after a few days it gradually developed into a mycelium that has a pinkish-tan coloration that got more brownish with time (up to two weeks). The powdery felt-like surface of the mycelium had the surface characteristics of a *Penicillium* sp. The organism was Gram positive, had small spores, and a compressed growth style initially suggesting that it was a *Streptomyces* sp. An examination of the isolate P-25-2-4 by environmental scanning electron microscopy revealed that the spores are borne on verticillate-like sporophores that are a series of obpyriform verticils arranged in a whorl like fashion mostly, but not exclusively, at a terminus of a hyphal strand (FIG. 2). The verticils are enteroblastic conidiogenesis cells approximately 5.2-5.7µ in length to 1.6µ in diameter at the widest point. The individual spores are lemon shaped, ranging from 2.7-2.8µ in length to 1.5-1.6µ in diameter (FIG. 2). Furthermore, organisms having a verticillate-like fruiting habit have been placed in the group Streptoverticillum (Williams et al., 1989, supra) (FIG. 2). A close look at the morphology of these organisms reveals that none have a sporulation pattern that is identical to isolate P-25-2-4 (Williams et al., 1989, Bergey's Manuel of Systematic, *Bacteriology* 4: 2492-2508.).

Isolate P-25-2-4 was further studied for molecular relatedness to other organisms in the *Streptomyces* and other bacterial groups. A partial 16s rDNA clone of this organism was PCR amplified and sequenced, using standard methods (GenBank accession No. AY327845). The sequence was blasted against the GenBank data base and it possessed close similarity to some members of the family actinomycetales. In addition, there was 94% homology (642/682) between its partial 16s rDNA and that of *Streptomyces caelestis* (previously described as a streptoverticillum). Other organisms showing a high degree homology were *Kocuria kristinae* (99%) and *Rothia amarae* (94%). Interestingly even though isolate P-25-2-4 morphologically fit into the streptverticillium group, on a molecular basis, the genus *Streptoverticillum* has been unified into the genus *Streptomyces* (Witt and Stackebrandt, 1990, *System. & Appl. Microbiol.* 13: 361-371). Isolate P-25-2-4 was deposited as *Streptomyces* sp. culture no. MSU-2110 with the Montana State University culture collection. Culture no. 2110 was also deposited with the Agricultural Research Service Patent Culture Collection, Northern Regional Research Center, 1815 University Street, Peoria, Ill., 61604, as NRRL 30701, with a deposit date of Jan. 20, 2004.

The methods used in the present invention to isolate *Streptomyces* sp. NRRL 30701 are applicable to the discovery of numerous other slow growing streptomycetes found in higher plants. The successful isolation of representatives of this important group of microorganisms, as endophytes of higher plants, thus provides a new source of biologically active products. Strains of streptomycetes as sources for biological activity can be obtained from a diverse array of dicotyledonous plants including, in addition to *Monstera* sp., but not limited to, *Kennedia nigriscans*, *Ceiba pentandra*, *Chiliotrichum diffusum*, *Desfontainia spinosa*, *Drymis winteri*, *Dunalia purpurea*, *Grevellia pteridifolia*, *Misodendrum punctulatum*, *Monstera speciosa*, *Nothofagus antartica*, *Nothofagus betuloides*, *Nothofagus pumilio*, *Podocarpus nubigena*, *Taxus wallichiana*, and *Theobroma cacao*.

Coronamycin

The present also relates to isolated coronamycins.

The Streptomycete designated *Streptomyces* sp. NRRL 30701 produces a chemically unique compound that is a peptide antibiotic, which has been designated "coronamycin." To isolate coronamycin, *Streptomyces* sp. may be fermented and the broth extracted with an organic solvent, e.g., methylene chloride, and the contents of the residue purified by bioassay guided high performance liquid chromatography using the fungus *Pythium ultimum* as the test organism. Coronamycins A, B, C, D, and E have masses of 1203.4, 1217.9, 1185.8, 1199.8, and 1233.5 daltons, respectively, by mass spectroscopy.

Amino acid analysis of coronamycin reveals that coronamycin comprises a peptide chain having component 1, component 2, tyrosine (Tyr), methionine (Met), and leucine (Leu). Component 1, tentatively identified as threonine, produces a baseline-resolved peak migrating immediately after threonine and before alanine. Component 2, tentatively identified as alpha-aminobutyric acid runs as a partially (~20%) resolved leading shoulder of alpha-aminobutyric acid. The molar ratios of the five components, component 1:component 2:tyrosine:methionine:leucine are 2:2:1:1:3, respectively.

In a preferred embodiment, coronamycin has UV absorbances at 208, 214, and a broad band at 270 nm with millimolar extiniction coefficients of 2.86, 2.03, and 0.23, respectively; HPLC retention time of 36.43 minutes on a Microsorb 100-5 C-18 column, 250×4.6 mm, using 20% acetonitrile:80% water for 90 minutes as an initial elution solvent programmed to a final concentration of 80% acetonitrile at a flow rate of 2 ml/minute; and MS/MS component ions of 1203.4, 1217.9, 1185.8, 1199.8, and 1233.5 daltons.

The structural relatedness of the MS/MS component ions of 1203.4, 1217.9, 1185.8, 1199.8, and 1233.5 daltons is suggested by the concise and consistent amino acid analytical data (Table 1). The LC/MS/MS analysis provided evidence that the MS/MS component ions of 1203.4, 1217.9, 1185.8, 1199.8, and 1233.5 daltons of coronamycin were all related by virtue of having the same major fragments after MS/MS of the individual components. As an example, MS/MS of component ions 1217, 1203 and 1233 each yielded daughter ions at 435, 546, 631, and 960 suggesting the existence of a common core structure.

Figure 4:
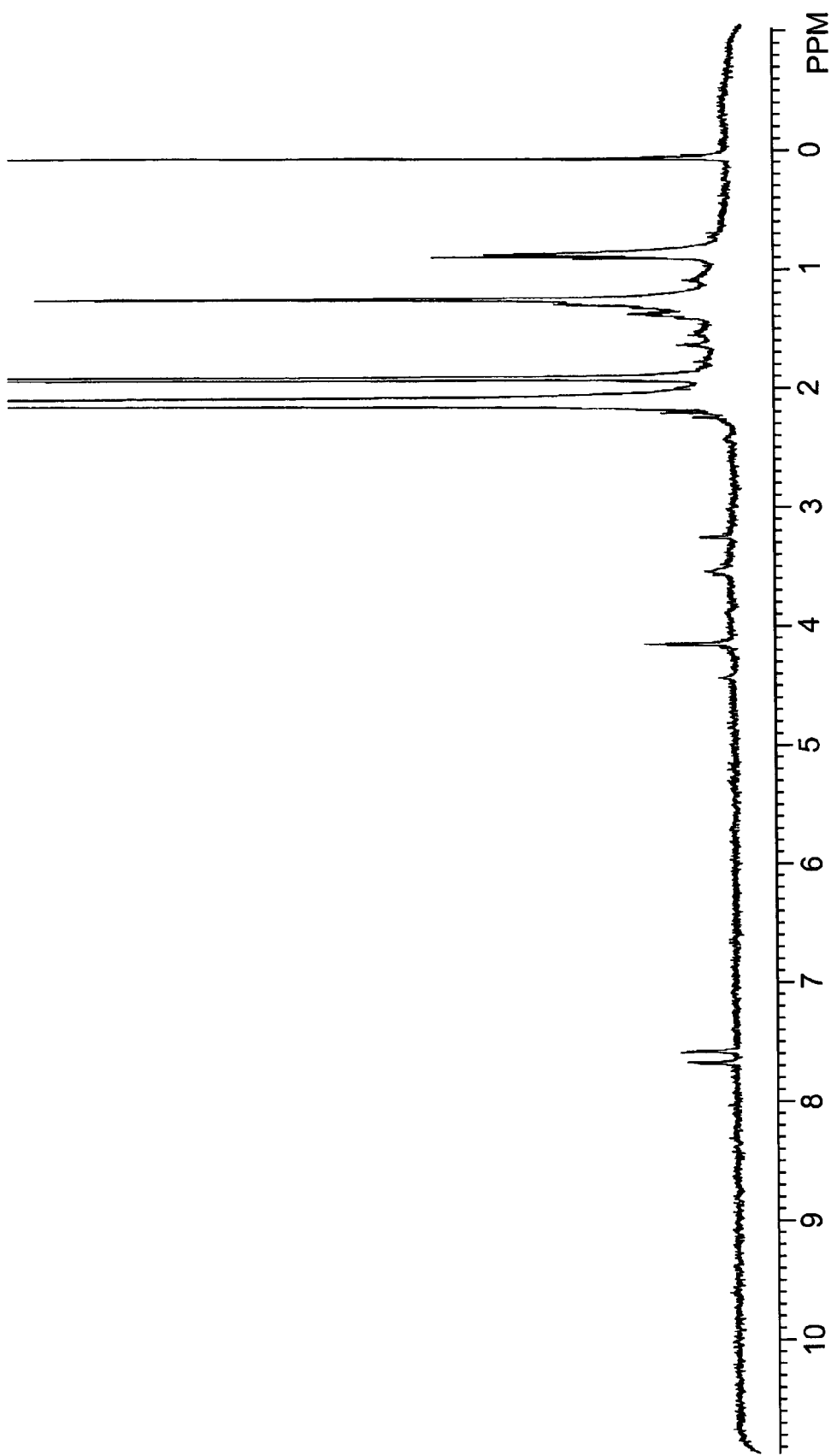
FIG. 4 shows the $^1$H NMR spectrum of coronamycin (deuterated acetonitrile, 500 MHz).

In a preferred embodiment, the $^1$H NMR spectrum (CDCl$_3$, 500 MHz) of purified coronamycin comprises $^1$H chemical shifts shown in FIG. 4.

Coronamycin is against the malarial parasite *Plasmodium falciparum* with IC$_{50}$ values at 9±7.3 ng ml$^{-1}$. The IC$_{50}$ of coronamycin is defined as the concentration of compound which yields 50% viability. The low IC$_{50}$ values of coronamycin are in the same range as chloroquine, the gold standard antimalarial compound, which has an IC$_{50}$ at 7.0 ng ml$^{-1}$. Since antimalarial compounds are effective in inhibiting proin and proin caused diseases in cell line assays, coronamycin is likely effective against such agents, e.g., the one that causes Mad Cow disease.

Coronamycin is also active against the pythiaceous organisms such as *Pythium ultimum*, with an MIC value of 2 µg ml,$^{-1}$ and related oomycetes such as *Apahanomyces cochlioides* and *Phytophthora cinnamomi*. The MIC (minimum inhibitory concentration) is defined as that concentration of a compound resulting in no visible growth of the test organism. Other plant pathogenic fungi, representing the three major families of plant pathogens, were not nearly as sensitive to coronamycin as *Pythium* or *Aphanaomyces* (Table 2).

Coronamycin is also active against the gram positive bacterium *Streptococcus pneumoniae* (ATCC 10031), but not other bacteria including *Pseudomonas aeruginosa* (ATCC 27853), *Klebsiella pneumoniae* (ATCC 10031), *Enterococcus faecium* (ATCC 49624), *Staphylococcus aureus* (ATCC 29213), and *Enterococcus faecalis* VRE (ATCC 51299).

Coronamycin displays activity against a number of human fungal pathogens. The most sensitive pathogen to coronamycin was *C. neoformans* having an MIC of 4.0 µg ml$^{-1}$ at 72 hrs (Table 3). However, the MIC was 0.065 µg ml$^{-1}$ at 48 hours for *C. neoformans*. It is apparent that this organism is sensitive to coronamycin whereas most of the other yeasts tested have MICs greater than 16 µg ml$^{-1}$ (Table 3).

Cytotoxicity testing of coronamycin against a primary mammary epithelial cell line (HMEC) gave an IC$_{50}$ of 2 µg ml$^{-1}$ whereas, taxol yielded a value of 25-30 µg ml$^{-1}$. In the case of the breast cancer cell line (BT20), coronamycin had an IC$_{50}$ of 1 µg ml$^{-1}$ whereas taxol was 0.009 µg ml$^{-1}$.

The coronamycins can, therefore, be used to treat or protect plants challenged or infected by an entire series of plant pathogens, and may be used to treat diseases in the field, soil or in post harvest applications. Similarly, the coronamycins are useful as agents to treat certain pathogenic conditions, from cancer to infections by bacterial, fungal, viral and parasitic pathogens of animals. Coronamycins have relevance to human medicine and drug discovery as the coronamycins show activity against a range of important diseases including tuberculosis, malaria, and certain diseases caused by Gram positive bacteria.

The present invention also relates to biologically active agents useful in treating or preventing various conditions. The biologically active agents can be the *Streptomyces* strains themselves, crude extracts obtained by cultivating such strains under culture conditions, or compounds isolated from the strains. In this manner the invention also provides novel biologically active extracts and compounds.

The biologically active agents of the present invention can be used to control a range of pathogenic organisms, diseases, or conditions. The agent is provided in an amount effective to inhibit the pathogenic organism or condition for a time and under conditions permitting the agent to inhibit the pathogenic organism or condition.

In a preferred embodiment, the biologically active agents can be used to control malaria.

In a preferred embodiment, the biologically active agents can be used to control parasitic organisms, including, but not limited to, infections caused by Gram positive bacteria and also some Gram negative bacteria. In a more preferred embodiment, the compounds are useful in the control of a parasitic *Plasmodium* spp., for example, *Plasmodium falciparum* and *Plasmodium vivax*. In a most preferred embodiment, the compounds are useful in the control of malarial parasite *Plasmodium falciparum*.

In another preferred embodiment, the biologically active agents can be used to control bacterial pathogens. Pathogenic bacterial organisms which may be controlled by the biological agents include, but are not limited to, strains of *Escherichia coli, Shigella dysenteriae, Pseudomonas syringae, Burkholderia cepacia, Acinetobacter boumanii, Apahanomyces cochlioides, Neisseria gonorrhoeae, Haemophilus influenzae, Stenotrophomas maltophilia, Staphylococcus* spp., *Staphylococcus aureus* MRSA, *Staphylococcus aureus* GISA, *Streptococcus pneumoniae, Enterococcus* spp., *Enterococcus faecalis, Mycobacterium* spp., *Mycobacterium tuberculosis, Bacillus anthracis, Erwinia carotovora, Vibrio fischeri, Streptococcus* spp., and *Acinetobacter* spp.

In another preferred embodiment, the biologically active agents can be used to control diverse fungal pathogens including, but not limited to, *Pythium ultimum, Rhizoctonia solani, Aspergillus* spp., *Aspergillus fumigatus, Fusarium oxysporum, Botrytis alli, Alternaria helianthi, Phytophthora infestans, Penicillum* sp., *Sclerotinia sclerotiorum, Cryptococcus neoformans, Histoplama capsulatum, Blastomyces dermatitidis, Cochliobolus carbonum, Geotrichum candidum, Phytophthora cinnamomi, Rhizoctonia solani, Candida tropicalis, Candida globrata*, and *Candida albicans, Candida tropicalis,* and *Candida parapsilosis.*

In another preferred embodiment, the biologically active agents can be used to protect against viral pathogens, or against an array of invertebrate pathogens.

In another preferred embodiment, the endophytic streptomycetes strains produce compounds having biological activity against cancer cells, and can be used in the treatment of cancer. Such cancer cells include, but are not limited to, human lung cancer epithelial A549 cells, human cervical cancer epithelial ME180 cells, and human breast cancer epithelial BT-20 cells.

Methods of Production

The present invention also relates to methods for producing a biological agent of the invention. The biological agent may be an endophytic Streptomycete; an extract of the endophytic Streptomycete, or a compound obtained from the endophytic Streptomycete, e.g., coronamycin, having the biological activity of interest. The methods comprise cultivating a strain of an endophytic *Streptomyces* spp. and recovering the biological agent from the culture medium. If the biological agent is a coronamycin, it may be desirable thereafter to form the free acid or a salt or ester by methods known per se.

The endophytic *Streptomyces* sp., or a high yielding or otherwise modified mutant thereof, may be used in the methods of the present invention to produce the biologically active agents.

The endophytic *Streptomyces* spp. are cultivated in a nutrient medium suitable for production of the heterologous biological substance using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the biological substance to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

When used herein, the term "cultivation" means the growth of an endophytic *Streptomyces* spp. in the presence of assimilable sources of carbon, nitrogen and mineral salts. Such aerobic growth may take place in a solid or semi-solid nutritive medium, or in a liquid medium in which the nutrients are dissolved or suspended. The cultivation may take place on a surface or by submerged culture. The nutritive medium may be composed of complex nutrients or may be chemically defined.

The nutrient media which may be used for the cultivation of the endophytic Streptomyces spp. may contain, in the range 0.1-10%, a complex organic nitrogen source such as yeast extract, corn steep liquor, vegetable protein, seed protein, hydrolysates of such proteins, milk protein hydrolysates, fish and meat extracts, and hydrolysates such as peptones. Alternatively, chemically defined sources of nitrogen may be used such as urea, amides, single or mixtures of common amino acids such as valine, asparagine, glutamic acid, proline, and phenylalanine. Carbohydrate (0.1-5%) may be included in the nutrient media and starch or starch hydrolysates such as dextrin, sucrose, lactose or other sugars or glycerol or glycerol esters may also be used. The source of carbon may also be derived from vegetable oils or animal fats. Carboxylic acids and their salts can be included as a source of carbon for growth and production of beta-lactamase inhibitors. A particularly suitable low cost medium is one containing soya bean flour plus dried malt distillers solubles plus dextrin.

Mineral salts such NaCl, KCl, $MgCl_2$, $ZnCl_2$, $FeCl_3$, $Na_2SO_4$, $FeSO_4$, $MgSO_4$ and $Na^+$ $^{K+}$ salts of phosphoric acid may be added to the media described above particularly if chemically defined. $CaCO_3$ may be added as a source of $Ca^{++}$ ions or for its buffering action. Salts of trace elements such as nickel, cobalt or manganese may also be included. Vitamins may be added if desired.

The present invention is also directed to a mutant of an endophytic Streptomyces wherein the amount of the coronamycin produced by the mutant is greater than the amount of the substance produced by a corresponding parental strain. The present invention is further directed to methods for obtaining such a mutant. A "parental strain" as defined herein is the original endophytic Streptomyces strain before mutagenesis which leads to the mutated strain. The term "mutant" includes any mutant strain which arises spontaneously or through the effect of an external agent whether that agent is applied deliberately or otherwise.

In one embodiment, a coronamycin of the present invention is obtained from a mutant of an endophytic Streptomyces strain, particularly, Streptomyces strain NRRL 30701, wherein the substance is produced in an amount greater than the amount of the substance produced by a corresponding parental strain. Suitable methods of producing mutant strains are well-known to those in the art, and include, for example, ionizing radiation (such as gamma-rays or X-rays), UV light, UV light plus a photosensitizing agent (such as 8-methoxypsoralen), nitrous acid, hydroxylamine, purine or pyrimidine base analogues (such as 5-bromouracil and N-methyl-N'-nitro-N-nitrosoguanidine), acridines, alkylating agents (such as mustard gas, ethyl-methane sulphonate), hydrogen peroxide, phenols, formaldehyde, and heat. Alternatively, mutants may be produced through genetic techniques such as recombination, shuffling, transformation, transduction, lysogenisation, lysogenic conversion, and selective techniques for spontaneous mutants. Specifically, one method of mutating an endophytic Streptomyces strain and selecting such a mutant comprises the following procedure: (i) the parental strain is treated with a mutagen; (ii) the thus presumptive mutants are grown in a medium suitable for selection of a mutant strain; and (iii) the mutant strain is selected on the basis of increased production of a compound of the present invention.

According to a preferred embodiment of this method, the selected colonies are grown in a normal production medium, and a final selection for such mutants is performed.

The present invention also relates to methods for obtaining "substantially pure" coronamycin of the present invention. "Substantially pure" coronamycin is defined herein as coronamycin which contains less than 5% contaminants. Coronamycin of endophytic Streptomyces spp. may be extracted from the culture filtrate by a variety of methods known to the art. The cells of the Streptomyces spp. are normally first removed from the fermentation by filtration or centrifugation before such extraction procedures are commenced. Precipitation by solvent extraction from culture filtrate, which may use an adjusted to acid pH values and methods based on the anionic nature of the metabolite such as the use of anion exchange resins may be utilized. Other primary methods of isolation which may be used include conventional methods such as adsorption onto carbon, precipitation, salting out, molecular filtration, or any method known in the art.

Compositions and Uses

The present invention also relates to compositions comprising a biological agent of the invention. The biological agent may be an endophytic Streptomycete, an extract of the endophytic Streptomycete, or a compound obtained from the endophytic Streptomycete, e.g., coronamycin, having the biological activity of interest. The composition can include a suitable carrier, or may comprise the agent affixed to a substrate. The compositions comprising a biologically active agent of the present invention can be used to control a range of pathogenic organisms, diseases, or conditions. The composition may also find use as applied to a substrate. The agent is provided in an amount effective to inhibit the pathogenic organism or condition for a time and under conditions permitting the agent to inhibit the pathogenic organism or condition. Different compositions will be required for administration to plants, humans and animals in unit dosage forms, such containing suitable quantities of the compounds.

Common carriers and excipients include, but are not limited to, corn starch or gelatin, lactose, sucrose, microcrystalline cellulose, kaolin, mannitol, dicalcium phosphate, sodium chloride, and alginic acid.

Coronamycin, or a salt or ester thereof, obtainable from an endophytic *Streptomyces* spp. can be formulated into a pharmaceutical composition, which comprises the compound, together with a pharmaceutically acceptable carrier.

The compound may be in the form produced by the endophytic *Streptomyces* spp., or the result of further chemical modification, for instance to reduce toxicity and perhaps to increase efficacy. This approach has been effectively taken with another antibiotic family, obtained from a plant associated microbe—*Pseudomonas syringae,* namely, the pseudomycins (Ballio et al., 1994*, FEBS Lett.* 355: 96-100). A specific pseudomycin has been subjected to modifications by organic synthesis and has yielded a derivative that is no longer toxic to mammalian systems and yet remains effective against human pathogenic fungi (Zhang et al., 2001*, Biorganic & Medicinal Chemistry* 11: 123-126; Zhang et al., 2001*, Biorganic & Medicinal Chemistry* 11: 903-907). Since coronamycin has numerous functional groups, especially those associated with the peptide portion of the molecule, such chemical derivatization would be an option.

The pharmaceutical compositions of the invention include those in a form adapted for oral, topical, or other potential use, and may be used for the treatment of infection in mammals including humans.

Examples of suitable unit dosage forms in accord with the present invention are tablets, capsules, pills, suppositories, powder packets, wafers, granules, cachets, teaspoonfuls, tablespoonfuls, dropperfuls, ampoules, suspensions, syrups, vials, aerosols with metered discharges, segregated multiples of any of the foregoing, and other forms as herein described. Such compositions may contain conventional pharmaceutically acceptable materials such as diluents, binders, colours, flavours, preservatives, disintegrants and the like in accordance with conventional pharmaceutical practice in the manner well understood by those skilled in the art of formulating antibiotics. The concentration of a compound in the unit dosage may vary, for example, from about 1 percent to about 50 percent depending on the particular form of the compound and its solubility and the dose desired.

For oral administration, either solid or fluid unit dosage forms can be prepared. For preparing solid compositions such as tablets, the desired compound is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Disintegrators commonly used in the compositions of the invention include croscarmellose, microcrystalline cellulose, corn starch, sodium starch glycolate, and alginic acid. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum, or other inert oil.

Fluid unit dosage forms for oral administration such as syrups, elixirs, and suspensions can also be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose, and the like.

Tablet binders that can be included are acacia, methylcellulose, sodium carboxymethylcellulose, poly-vinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils, and colloidal silica.

Flavoring agents such as peppermint, oil of wintergreen, cherry flavoring, or the like can also be used. It may be desirable to add a coloring agent to make the dosage form more attractive in appearance or to help identify the product.

For parenteral administration, fluid unit dosage forms are prepared utilizing the compound and a sterile vehicle, with water being preferred. The compound, depending on the vehicle and concentration used, can be either suspended or dissolved in the vehicle. In preparing solutions, the compound can be dissolved in water for injection and filtered sterilized before filling into a suitable vial or ampoule and sealing. Advantageously, adjuvants such as a local anesthetic, preservative, and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the antibiotic.

Additionally, a rectal suppository can be employed to deliver the compound. This dosage form is of particular interest where the mammal cannot be treated conveniently by means of other dosage forms, such as orally or by insufflation, as may be the case of animals, or young children, or debilitated persons. The antibiotic can be incorporated into any of the known suppository bases using methods known in the art. Examples of such bases include cocoa butter, polyethylene glycols (carbowaxes), polyethylene sorbitan monostearate, and mixtures of these with other compatible materials to modify the melting point or dissolution rate. These rectal suppositories can weigh from about 1 to 2.5 gm.

The term "unit dosage form" is defined herein as physically discrete units suitable as unitary dosages for human subjects and animals, each unit containing a predetermined quantity of active material calculated to produce the desired pharmaceutical effect in association with the required pharmaceutical diluent, carrier, or vehicle. The specifications for the novel unit dosage forms of the invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

Typically, any effective quantity of a compound of the present invention is employed in treatment. The determination of an appropriate dosage of the compound for a given treatment depends on many factors that are well known to those skilled in the art. They include for example, the route of administration and the potency of the particular compound.

The particular compound may be present in the composition as the sole therapeutic agent or may be present together with other therapeutic agents, either related or unrelated to the original compound.

A convenient method of practicing the treatment method may be to administer a compound of the present invention via intravenous infusion. In this procedure a sterile formulation of a suitable soluble salt of the compound is incorporated in a physiological fluid, such as 5% dextrose solution, and the resulting solution is infused slowly IV. Alternatively, the piggy-back method of IV infusion can also be used. For intravenous IV use, a water soluble form of the antibiotic can be dissolved in one of the commonly used intravenous fluids and administered by infusion. Such fluids as, for example, physiological saline, Ringer's solution, or 5% dextrose solution can be used.

For intramuscular preparations, a sterile formulation of a suitable soluble salt form of the compound, for example the hydrochloride salt, can be dissolved and administered in a pharmaceutical diluent such as pyrogen-free water (distilled), physiological saline or 5% glucose solution. A suitable insoluble form of the compound may be prepared and administered as a suspension in an aqueous base or a pharmaceutically acceptable oil base, for example, an ester of a long chain fatty acid such as ethyl oleate.

A composition comprising a compound of the present invention can be administered in a single daily dose or in multiple doses per day. The treatment regimen may require administration over extended periods of time, for example, for several days or from one to six weeks. The amount per administered dose or the total amount administered will depend on such factors as the nature and severity of the infection, the age and general health of the patient, the tolerance of the patient to the antibiotic and the microorganism or microorganisms involved in the infection.

Catheter infections may lead to severe complications for a patient, and, even if they are not life-threatening, they may contribute to a prolongation of hospital stay and to an increase in therapy costs. Most of the catheter infections can be managed by removing the catheter if clinical signs of infection occur; this is normal clinical routine procedure in patients having short peripheral venous lines. Gram-positive bacteria like *Staphylococcus aureus* and coagulase negative staphylococci (CNS) are the predominant causative organisms.

A further object of the present invention is a method of preventing catheter related infections in a patient in need of application of a central venous catheter, such method consisting in the insertion into the patient of a central venous polyurethane catheter with a thin hydrophilic layer on the surfaces loaded with a compound of the present invention. Central venous polyurethane catheters with a thin hydrophilic layer on the surfaces loaded with a compound of the present invention, may be effective in inhibiting development of bacterial colonization and preventing catheter related infections after the insertion into the patients. The present invention provides a central venous polyurethane catheter with a thin hydrophilic layer on the surfaces loaded with a compound of the invention, in a concentration sufficient to inhibit the bacterial colonization of the catheter after its insertion into the patient. Catheters particularly suitable for use in the invention are polyurethane catheters with a thin hydrophilic coating on both the internal and external surface based on a poly-N-vinylpyrrolidone-polyurethane interpolymer of approximately 200 micron thickness. The catheters of the invention can be maintained in place for the desired period without incurring severe complications for the catheterized patient.

Compositions as described may be used for the treatment of infections of inter alia, the respiratory tract, the urinary tract, and soft tissues in humans. The compositions may also be used to treat infections of domestic animals such as mastitis in cattle.

Provided, then, are compositions and methods of treating bacterial infection in an organism, such as a plant or mammal, which comprises administering to the organism an antibacterially effective amount of a coronamycin, or a salt or ester thereof. The compositions can be used to control parasitic organisms, including, but not limited to, infections caused by Gram positive bacteria and also some Gram negative bacteria. In a preferred aspect, the compositions are useful in the control of a parasitic *Plasmodium* spp., for example, *Plasmodium falciparum* or *Plasmodium vivax*, which comprises administering to an infected human an effective amount of a coronamycin, or a salt or ester thereof.

The compositions can also be used to control bacterial pathogens. Pathogenic bacterial organisms which may be controlled by the compositions include, but are not limited to, strains of *Escherichia coli, Shigella dysenteriae, Pseudomonas syringae, Burkholderia cepacia, Acinetobacter boumanii, Neisseria gonorrhoeae, Haemophilus influenzae, Stenotrophomas maltophilia, Staphylococcus* spp., *Staphylococcus aureus* MRSA, *Staphylococcus aureus* GISA, *Streptococcus pneumoniae, Enterococcus* spp., *Enterococcus faecalis, Mycobacterium* spp., *Mycobacterium tuberculosis, Bacillus anthracis, Erwinia carotovora, Vibrio fischeri, Streptococcus* spp., and *Acinetobacter* spp.

Also provided are compositions and methods of treating fungal infection in an organism, such as a plant or mammal, which comprises administering to the organism an antifungal, effective amount of a coronamycin, or a salt or ester thereof.

The compositions can also be used to control diverse fungal pathogens including, but not limited to, *Pythium ultimum, Rhizoctonia solani, Aspergillus* spp., *Aspergillus fumigatus, Fusarium oxysporum, Botrytis alli, Alternaria helianthi, Phytophthora infestans, Penicillum* sp., *Sclerotinia sclerotiorum, Cryptococcus neoformans, Histoplama capsulatum, Blastomyces dermatitidis, Cochliobolus carbonum, Geotrichum candidum, Phytophthora cinnamomi, Rhizoctonia solani, Candida tropicalis, Candida globrata,* and *Candida albicans, Candida tropicalis,* and *Candida parapsilosis.*

The compositions can also be used to protect against viral pathogens, or against an array of invertebrate pathogens.

The compositions can also be used in the treatment of cancer. Such cancer cells include, but are not limited to, human lung cancer epithelial A549 cells, human cervical cancer epithelial ME180 cells, and human breast cancer epithelial BT-20 cells.

In a further aspect, the present invention provides a method for treating infectious diseases, especially those caused by Gram-positive microorganisms, in animals. The compounds of the present invention are particularly useful in treating infections caused by *Staphylococcus, Enterococcus,* and *Streptococcus* species. Also, the compounds are useful in treating infection due to *Listeria monocytogenes, Vibrio fischeri,* and *Bacillus anthracis.* Examples of such diseases are community acquired pneumonia, nosocomial infections such as ventilator associated pneumonia, and bacterimia. The animal may be either susceptible to, or infected with, the microorganism. The method comprises administering to the animal an amount of a compound of the present invention which is effective for this purpose. In general, an effective amount is a dose between about 0.5 and about 100 mg/kg. A preferred dose is from about 1 to about 60 mg/kg of active compound. A typical daily dose for an adult human is from about 50 mg to about 5 g.

Compounds derived from endophytic *Streptomyces* spp. may also be used to promote growth in meat-producing animals such as broiler chicks, swine, and cattle. The determination of the appropriate amounts and procedures for the use of the antibiotics of the present invention to promote growth in meat-producing animals would be well-known to one of ordinary skill in the art.

The compositions of the invention may be pesticidal compositions used for administration to plants, or the associated soil. For use with a plant, the method may involve applying an endophytic Streptomycete strain, or an extract or compound derived from the strain either directly to the plant, or to soil adjacent to the plant. In some cases the treatment may be made to seeds. In certain circumstances, the strain can be applied to grow in association with the plant and produce the biologically active compounds capable of protecting the plant against plant pathogen attack.

The present invention is further directed to pesticidal compositions comprising the substance in an effective amount to control a pest and a pesticidal carrier. "Effective amount" is defined herein as the amount of the substance sufficient to control a pest through killing or stunting of the growth of the pest or protecting a plant from pest infestation. The pesticidal compositions may comprise a compound of the present invention in a substantially pure form or as an extract from a whole broth culture of an endophytic Streptomycete in dry, concentrated, or liquid form and a suitable pesticidal carrier, examples of which are disclosed infra. The substance is present in the composition at a concentration of from about 0.001% to about 60% (w/w).

The pesticidal compositions may further comprise a deposition agent which assists in preventing the composition from drifting from the target area during application (e.g., as it is sprayed from a plane), or from being blown away from the plant once it has been deposited. The deposition agent in the compositions of the present invention is preferably a proteinaceous material, which has the added benefit of being palatable to the insect. Any animal or vegetable protein is suitable for this purpose, in dry or in liquid form. Examples of useful sources of protein which can be conveniently and economically added to the composition include, but are not limited to, soy protein, potato protein, soy flour, potato flour, fish meal, bone meal, yeast extract, and blood meal. Alternative deposition agents include modified cellulose (carboxymethylcellulose), botanicals (grain flours, ground plant parts), non-phyllosilites (talc, vermiculite, diatomaceous earth), natural clays (attapulgite, bentonite, kaolinite, montmorillonite), and synthetic clays (Laponite). When utilized, the deposition agent is present in the pesticidal compositions of the present invention in an amount of between about 0.4% w/w and about 50% w/w, preferably between about 1% w/w and about 20% w/w.

The pesticidal compositions may further comprise an antifreeze/humectant agent which suppresses the freeze point of the product and helps minimize evaporation when sprayed and which maintains deposit texture making the product more efficacious and palatable. Examples of antifreeze/humectant agents include, but are not limited to, ethylene glycol, propylene glycol, dipropylene glycol, glycerol, butylene glycols, pentylene glycols and hexylene glycols. When utilized, the antifreeze/humectant agent is present in the pesticidal compositions of the present invention in an amount of between about 0.5% w/w and about 25% w/w, preferably between about 2% w/w and about 15% w/w.

The pesticidal compositions may further comprise a surfactant in an amount where it acts as an emulsifying, a wetting, or a dispersing agent. Examples of such surfactants are anionic surfactants such as carboxylates, for example, a metal carboxylate of a long chain fatty acid; N-acylsarcosinates; mono or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g., butyl naphthalene sulphonate; salts or sulphonated naphthalene-formaldehyde condensates; salts of sulphonated phenol-formaldehyde condensates; or more complex sulphonates such as amide sulphonates, e.g., the sulphonated condensation product of oleic acid and N-methyl taurine or the dialkyl sulphosuccinates, e.g., the sodium sulphonate or dioctyl succinate. Further examples of such surfactants are non-ionic surfactants such as condensation products of fatty acid esters, fatty alcohols, fatty acid amides or fatty-alkyl- or alkenyl-substituted phenols with ethylene oxide, block copolymers of ethylene oxide and propylene oxide, acetylenic glycols such as 2,4,7,9-tetraethyl-5-decyn-4,7-diol, or ethoxylated acetylenic glycols. Further examples of such surfactants are cationic surfactants such as aliphatic mono-, di-, or polyamine as acetates, naphthenates or oleates; oxygen-containing amines such as an amine oxide of polyoxyethylene alkylamine; amide-linked amines prepared by the condensation of a carboxylic acid with a di- or polyamine; or quaternary ammonium salts. When utilized, the surfactant is present in an amount of between about 0.5% w/w and about 25% w/w, preferably between about 1% w/w and about 8% w/w.

The pesticidal compositions may further comprise an inert material. Examples of inert materials include inorganic minerals such as diatomaceous earth, kaolin, mica, gypsum, fertilizer, phyllosilicates, carbonates, sulfates, or phosphates; organic materials such as sugars, starches, or cyclodextrins; or botanical materials such as wood products, cork, powdered corncobs, rice hulls, peanut hulls, and walnut shells.

The pesticidal compositions may further comprise a preservative, a feeding stimulant, an attractant, an encapsulating pesticide, a binder, a dye, an ultraviolet light protectant, a buffer, a flow agent, or other component to facilitate product handling and application for particular target pests.

The pesticidal compositions can be applied in a dry or liquid form, e.g., a suspension, a solution, an emulsion, a dusting powder, a dispersible granule, a wettable powder, an emulsifiable concentrate, an aerosol or impregnated granule, or a concentrate or primary composition which requires dilution with a suitable quantity of water or other diluent before application. The concentrations of each component in the composition will vary depending upon the nature of the particular composition, specifically, whether it is a concentrate or to be used directly. The composition may contain about 1% to about 98% of a solid or liquid inert carrier. The compositions will be preferably administered at the labeled rate for commercial products, preferably about 0.01 pound to 5.0 pounds per acre when in dry form and at about 0.01 pint to 25 pints per acre when in liquid form.

The pesticidal compositions can be applied directly to a plant by, for example, spraying or dusting at the time when the pest has begun to appear on the plant or before the appearance of pests as a protective measure. The pesticidal compositions can be applied by foliar, furrow, broadcast granule, "lay-by", or soil drench application. The compositions can also be applied directly to ponds, lakes, streams, rivers, still water, and other areas subject to infestation by pests of concern to public health. The compositions can be applied by spraying, dusting, sprinkling, or the like. The spray or dust can conveniently contain another pesticide. The pesticidal compositions are preferably applied directly to the plant.

The pesticidal compositions can be applied to protect a number of different plant types, including, but not limited to, cereals (wheat, barley, rye, oats, rice, sorghum and related crops), beets (sugar beet and fodder beet), drupes, pomes and soft fruit (apples, pears, plums, peaches, almonds, cherries, strawberries, raspberries, and blackberries), leguminous plants (alfalfa, beans, lentils, peas, soybeans), oil plants (rape, mustard, poppy, olives, sunflowers, coconuts, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages and other brassicae, carrots, onions, tomatoes, potatoes), lauraceae (avocados, cinnamon, camphor), deciduous trees and conifers (linden-trees, yew-trees, oak-trees, alders, poplars, birch-trees, firs, larches, pines), or plants such as maize, turf plants, tobacco, nuts, coffee, sugar cane, tea, vines, hops, bananas and natural rubber plants, as well as ornamentals.

The present invention is further described by the following examples, which should not be construed as limiting the scope of the invention.

EXAMPLES

Materials

All solvents used for HPLC were HPLC grade while solvents used for extraction were ACS grade. All other reagents were obtained from Sigma Chemical Co., St. Louis, Mo., including adrenocorticotropic hormone fragment 18-39, standard amino acids, and radiolabelled phenylalanine.

Example 1

Isolation and Identification of the Endophytes of *Monstera speciosa*

Stems (about 0.2-0.4 cm in diameter) of *Monstera speciosa* (FIG. 1) were obtained in the Lake Sandoval area of the Bahuaja Sonene Park Nacional in the upper Amazon region of Peru at 12° 36' 25" South and 69° 01' 54" W. The stems were thoroughly treated with 70% ethanol and then the outer bark removed with a sterilized sharp blade. The inner pieces of the stem, containing the cambium, phloem, and xylem tissues, were plated on water agar in Petri plates. After incubation for 10 or more days at 23° C., individual fungal and bacterial colonies were removed with a sterile fine tipped needle and transferred onto potato dextrose agar (PDA) composed per liter of 39 g of potato dextrose agar. The plates were continuously monitored for spore formation by stereo and light microscopy.

This organism was deposited as *Streptomyces* sp. P-25-2-4 as culture No. MSU-2110, of the Montana State University Mycological (MONT) culture collection. Small PDA pieces, mostly containing spores, were stored in 15% glycerol in water (v/v) at −70° C.

The isolation procedure above produced at least one microorganism that resembled a streptomycete. This organism was initially designated as P-25-2-4. This organism was not isolatable from any of a number of other trees and vines growing in the Lake Sandoval region of the upper Amazonian basin including *Heliconia* sp., *Piper* sp., *Philodendron* sp., *Ochroma pyramidale,* and *Caryota urens.* When transferred and grown on PDA, the organism produced a whitish fluffy mycelial growth after a few days it gradually developed into a mycelium that has a pinkish-tan coloration that got more brownish with time (up to two weeks). The powdery felt-like surface of the mycelium had the surface characteristics of a *Penicillium* sp. The organism was Gram positive, had small spores, and a compressed growth style initially suggesting that it was a *Streptomyces* sp.

Isolate P-25-2-4 was further studied for molecular relatedness to other organisms in this and other bacterial groups. Isolate P-2S-2-4 was grown on PDA in a 9 cm Petri plate for 14 days at 23° C. The colonies were scraped directly from the surface of the agar culture. Extraction of DNA was done with Qiagen's DNeasy mini kit according to the manufacturer's instructions (QIAGEN, Chatsworth, Calif.). A partial 16S rDNAfragrnent of about 920 bp was amplified from genomic DNA of isolate P-2S-2-4 via the polymerase chain reaction (PCR) using the bacterial primers: 16S-bact-27f (5'-AGA-GTT-TGA-TCM-TGG-CTC-AG-3', SEQ ID NO: 1) and 16S-bact-907r (5'-CCG-TCA-ATT-CMT-TTR-AGT-TT-3', SEQ ID NO: 2) (Lane, 1991, 16S/23S rDNA sequencing, In Nucleic Acid Techniques in Bacterial Systematics, (eds. E. Stackebrandt and M. Goodfellow), John Wiley, Chicester, pp. 115-176). The reaction (PCR) was performed in a 25 µl final volume containing 0.1 µg of genomic DNA, 10 mM of each primer, 3 mM of the 4 dNTPs, and 0.5 µg NovaTaq™ polymerase (Novagen, San Diego, Calif.) in Taq buffer (Novagen, San Diego, Calif.) containing 1.5 mM magnesium chloride. The following cycle parameters were maintained: 95° C. for 5 minutes followed by 34 cycles of 40 seconds at 95° C., 40 seconds at 50° C. and 40 seconds at 72° C. followed by 5 minutes at 72° C. The PCR product was purified and desalted using the QlAquick PCR purification kit (QIAGEN, Chatsworth, Calif.).

The PCR product was cloned into a pGem-T easy vector (Promega Madison, Wis., USA) according to manufacturer's instructions. Transformation of the cloned PCR product into *E.coli* DH5α was performed as previously described (Stinson et. al., 2003, *Plant Sci.* 165: 93-922). The transformed cells were plated on LB agar supplemented with 30 µg/ml ampicillin (Sigma Chemical Co., St. Louis, Mo.), in the presence of IPTG and X-gal for blue/white selection. White single colonies were grown in LB broth and DNA was extracted using a Perfectprep Plasmid Mini Kit (Eppendort) according to manufacturer's instructions. Presence of the insert was confirmed by DNA digestion with the restriction enzyme EcoRI (Promega, Madison, Wis.).

The plasmid inserts were sequenced by the Plant-Microbe Genomics Facility at Ohio State University using an Applied Biosystems 3700 DNA Analyzer and BigDye™ cycle sequencing terminator chemistry and the universal primers T7 and Sp6 designed for sequencing from pGem-T easy.

The 16s rDNA sequence was blasted against the GenBank data base and found to possess close similarity to some members of the family actinomycetales. In addition, there was 94% homology (642/682) between its partial 16s rDNA and that of *Streptomyces caelestis* (previously described as a streptoverticillum). Other organisms showing a high degree homology were *Kocuria kristinae* (99%) and *Rothia amarae* (94%). Interestingly even though isolate P-25-2-4 morphologically fit into the streptverticillium group, on a molecular basis, the genus *Streptoverticllum* has been unified into the genus *Streptomyces* (Witt and Stackebrandt, 1990, Unification of the genera *Streptoverticillum* and *Streptomyces* and amendation of the *Streptomyces* Waksman and Henrici 1943, 339$^{AL}$ *System. & Appl. Microbiol.* 13: 361-371). Isolate P-25-2-4 was, therefore, placed on deposit in the Montana State University culture collection as a *Streptomyces* sp. (MSU-2110).

Scanning electron microscopy was performed on the *Streptomyces* sp. isolate (MSU-2110) by placing agar pieces and as well as δ-irradiated carnation pieces supporting bacterial growth into #1 Whatman filter paper packets. The packets were made by folding the filter paper over a piece of cork (1.5 cm). The packets were tied with cotton string and two removable split shot sinkers (ca. 3.25 gm each) were attached next to the packets to hold them under the surface of the dehydrating solutions and the liquid carbon dioxide during critical point drying. The preparation was then placed into 2% glutaraldehyde in 0.1 M sodium cacodylate buffer (pH 7.2-7.4) with Triton X, a wetting agent, aspirated for 5 minutes and left overnight. The next day they were washed in 6 changes of water-buffer, followed by three 15 minute changes in 10% ethanol, four 15 minute changes of 30% ethanol, five 15 minute changes of 50% ethanol and left for two days in 70% ethanol. They were then rinsed in five 15 minute changes of 95% ethanol and then five 15 minute changes in 100% ethanol. The dehydration process was slowly done to discourage the processes of spore shriveling which may occur during rapid dehydration. Ultimately, the biological material was critically point dried, gold sputter coated and examined with a JEOL 6100 scanning electron microscope (SEM).

Because the fruiting structures of the bacterium appeared fragile and easily subjected to disruption, the organism was subjected to the relatively unique microscopic application which preserves the sporophore intact (spores attached). Thus, fresh or non-treated specimens were examined by environmental scanning microscopy and images were recorded with a Philips XL 30 ESEM FEG. A gaseous secondary electron detector was used with a spot size of 3, at 15 kV. The temperature was 4° C. with a chamber pressure which ranged from 5 to 6 Torr providing humidity from 80-100% at the sample.

The spores were borne on verticillate-like sporophores that were a series of obpyriform verticils arranged in a whorl-like fashion mostly, but not exclusively, at a terminus of a hyphal strand (FIG. 2). The verticils were enteroblastic conidiogenesis cells approximately 5.2-5.7µ in length to 1.6μ in diameter at the widest point. The individual spores were lemon shaped, ranging from 2.7-2.8μ in length to 1.5-1.6μ in diameter (FIG. 2). Furthermore, organisms having a verticillate—like fruiting habit have been placed in the group Streptoverticillum (Williams et al., 1989) (FIG. 2). A close look at the morphology of these organisms revealed that none have a sporulation pattern that is identical to P-25-2-4 (Williams, S. T., Sharpe, M. E., & Holt, J. G., [eds], 1989, *Bergey's Manuel of Systematic Bacteriology* 4, 2492-2508).

Example 2

Isolation Procedures for Coronamycin

*Streptomyces* sp. (MSU-2110) was grown as an even lawn on PDA plates for at least 7 days at 23° C. One quarter of the agar plate was used to inoculate 1 liter of PSNB medium in a 2 liter flask and the flask was left standing at 25° C. for 3 to 4 weeks. Potato Sucrose Agar Natural (PSNB) is a high nutrient medium with sucrose and natural potato pellets as carbon source (Basic American, Rexburg Id., USA). PSNB medium was composed per liter of 20 g of sucrose and 15 g of potato pellets. Thick pink-purple-brown layers of the organism developed on the surface of the liquid after 2 to 3 weeks.

For extraction of the secondary metabolites; the culture was filtered through two layers of cheesecloth and the filtrate was extracted three times with 0.5 equal volumes of methylene chloride. The organic solvent was pooled and dried under flash evaporation at 40° C. The yield of dried residue was about 150 mg per liter.

The dried residue was dissolved in 5 ml of chloroform and applied to a 3×15 cm column of Selecto silica gel (32-36 particle size; Selecto Scientific, Georgia, USA). The column was first rinsed with at least 200 ml of chloroform followed by a series of 100 ml of chloroform/methanol v/v mixtures in the following order: 200:1, 100:1, 50:1, 10:1, 9:1, 5:1, 4:1, 3:1, 2.5:1. Each fraction, after solvent evaporation, was tested for biological activity against *Pythium ultimum*.

The bioactive fractions obtained from the silica gel and HPLC columns were subjected to a bioassay test by introducing known amounts of the material to be tested dissolved in methanol and placed into the depressions of a 24 well test plate. After the evaporation of the solvent, 1 ml of potato dextrose broth (PDB) was added to the wells and a 2×3×3 mm block of PDA harboring the fungus P. ultimum was placed into each well and then monitored for growth as a function of time. The appropriate controls were performed during the course of each experiment. The MIC values were obtained at 48 hours and the first well in the plate, in the dilution series, showing no growth was taken as the MIC value.

Figure 3:
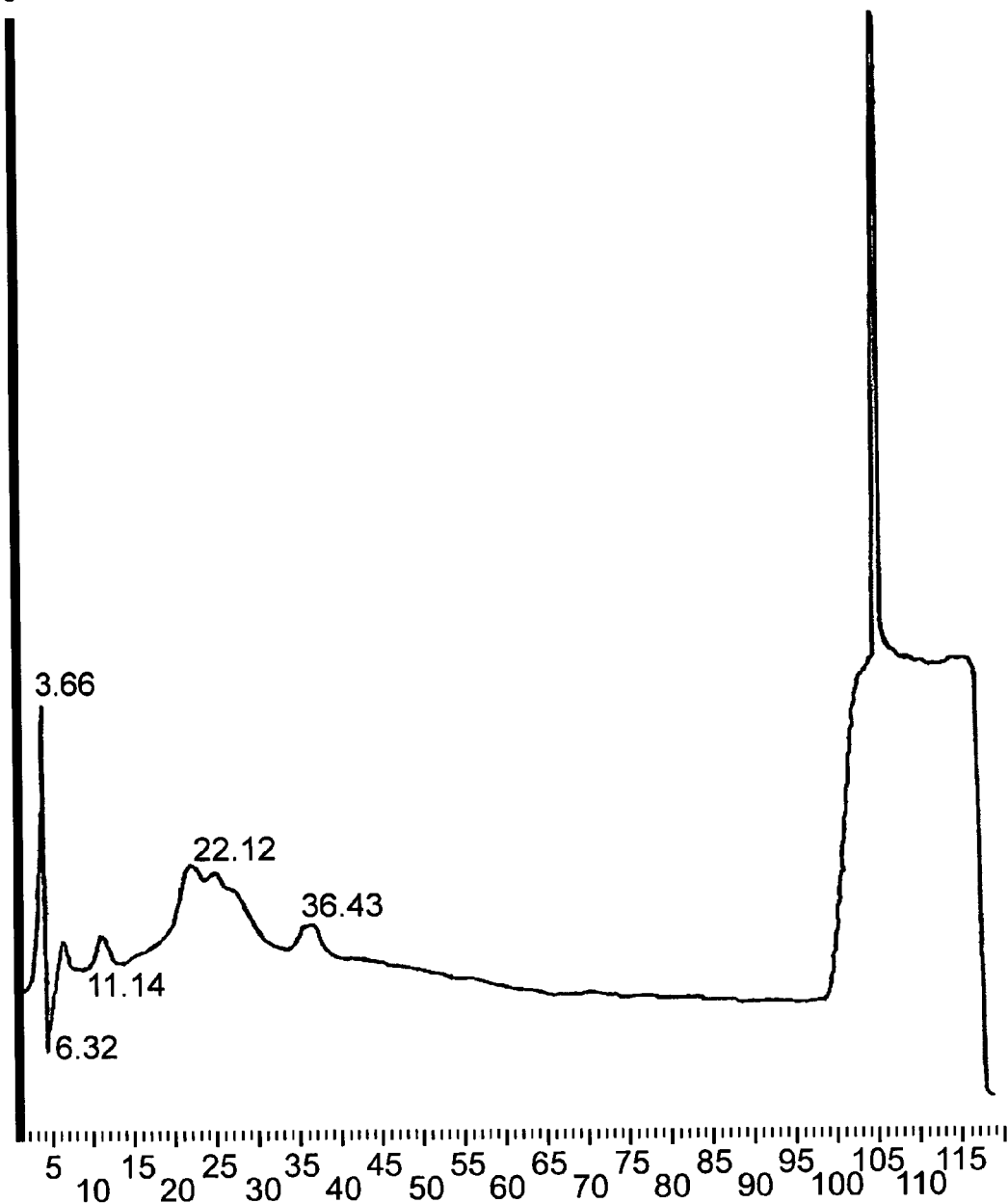
FIG. 3 shows an HPLC elution pattern of coronamycin on a Waters Symmetry 4.6×150 mm C-18 column (3.5 microns) using 60% methanol:40% water programmed to a final concentration of 65% methanol:35% water after 30 minutes; followed by 65% methanol:35% water programmed isocratically for 60 minutes with a final column wash with 100% methanol. The x axis shows UV absorption at 220 nm while the y axis shows time. The coronamycin eluted at 36.43 minutes

The last fraction (No. 9) was the only fraction active against the test organism. Approximately 1 mg of this material recovered from fraction 9 was subjected to High Pressure Liquid Chromatography (HPLC) on a Varian-Microsormv 100 Å, 250×10 mm, C-18 column. The elution solvent was 60% methanol: 40% water programmed to final concentration of 100% methanol after 60 minutes at a flow rate of 0.5 ml/minute. Formic acid (0.1%) was added to each of the solvents. The elution process was monitored at 280 mn. The major bioactive fraction eluted at 36.43 minutes (FIG. 3).

The bioactive material was then subjected to an additional HPLC step, monitiored at 220 run, with the same column. The elution solvents were 60% methanol:40% water programmed to a final concentration of 65% methanol:35% water after 30 minutes; followed by 65% methanol:35% water programmed isocratically for 60 minutes with a final column wash with 100% methanol. A biologically active peak eluted at 28 minutes This fraction was concentrated and then subjected to a final HPLC step utilizing a Waters Symmetry 4.6×150 mm, 3.5 μm, C-18 column under the same conditions as at the previous stage. A biologically active fraction eluted at 35-36 minutes. All together approximately 0.2 mg of this fraction was obtained per liter of bacterial culture fluid and this fraction was termed "coronamycin".

Example 3

Chemical Characterization of Coronamycin

Only final step HPLC preparations of the coronamycin were used to both chemically and biologically characterize the compound.

UV Spectrum. Analysis of the UV absorption spectrum of coronamycin, in methanol, produced peaks at 208 nm, 214 nm, and a broad band at 270 nm with millimolar extinction coefficients of 2.86, 2.03, and 0.23, respectively. The absorption band at 208 nm suggested the presence of amido chromophoric groups which would be consistent with the presence of one or more peptide bonds in the molecule (Silverstein et al., 1991, Spectrometric Identification of Organic Compounds. Wiley and Sons, New York). The broad band at 270 nm hinted at the presence of an aromatic moiety in the molecule (Silverstein, 1991, supra). The $^1$H NMR spectrum suggested that the primary nature of the coronamycin is that of a functionalized peptide (FIG. 4).

Amino acid analyses. The HPLC purified bioactive fraction of coronamycin was dissolved in 50% (v/v) methanol in water, placed in 6×50 mm glass tubes, dried in vacuo, and then transferred to a hydrolysis vessel (PN007603, Millipore, Marlborough, Mass., USA; part no. 007603). Approximately 300 μl of 6 N HCl were added to the vessel which was then alternatively purged with nitrogen and evacuated three times before being sealed under vacuum. Vapor phase hydrolysis was performed by heating at 110° C. for 22 hours. After cooling, the hydrolysis tubes were removed from the reaction vessel and dried in a centrifugal concentrator (SpeedVac, ThermoSavant, Holbrook, N.Y.) for 30 minutes. Samples then were derivatized and analyzed by pre-column 6-aminoquinolyl-N-hydroxysuccinimidyl carbamate (AQC) derivatization followed by reverse phase HPLC. An Alliance/Millenium HPLC system (Waters, Milford, Mass.) equipped with an AccQTag amino acid analysis column was used. The AQC chemistries were done according to the manufacturer's instructions. Moles of each amino acid were initially determined using molar absorption extinction coefficients derived from amino acid standards. All analyses were done at least twice on samples prepared from at least two individual fermentations of the microorganism.

Amino acid analysis of coronamycin revealed five major components (Table 1). The results are presented as the mean±SD of two individual amino acid analyses of the HPLC prepared coronamycin. The bolded number in parentheses following each amino acid residue indicates the tentatative number of moles of that residue per mole of coronamycin M.W. 1203 based on one mole percent being 11. These components chromatographed with retention times identical, within experimental error, to those of threonine, alpha-aminobutyric acid, tyrosine, methionine, and leucine.

TABLE 1

Amino acid composition of coronamycin

| Amino acid | Mole percentage of each amino acid |
| --- | --- |
| Component 1 | 22.12 ± 1.72 (2) |
| Component 2 | 24.50 ± 2.14 (2) |
| Tryosine | 10.38 ± 3.16 (1) |
| Methionine | 7.98 ± 0.76 (1) |
| Leucine | 34.22 ± 0.76 (3) |

When hydrolyzed coronamycin was combined with a mixture of amino acid standards prior to chromatography, the components identified as tyrosine, methionine, and leucine comigrated with their respective amino acid standard. However, the component tentatively identified as threonine produced a baseline-resolved peak migrating immediately after threonine and before alanine. This peak was termed "component 1." The component tentatively identified as alpha-aminobutyric acid ran as a partially (~20%) resolved leading shoulder of a-amino butyric acid. This peak was termed "component 2." The molar ratios of the five components, component 1:component 2:tyrosine:methionine:leucine were 2:2:1:1:3, respectively (Table 1). The amino acid detection system employs a fluorescent amino-reactive agent, therefore the unidentified components are amino compounds. In addition, these compounds are released by acid hydrolysis of the parent compound and are at least partially resistant to this treatment, suggesting they have chemical properties akin to those of amino acids. Unusual amino acids are commonly found in biologically active peptides produced by endophytes and on occasion these may have elution times close or identical to those of the standard amino acids (Ballio et al., 1994, FEBS Lett. 355: 96-100; Strobel et al., 1999, supra; Miller et al., 1998, J. Applied Microbiology 4: 937-944). In addition, the hydrolysis of peptides containing unusual amino acids can cause the elimination of labile substituent groups (e.g., dechlorination of chlorothreonine). This results in the production of amino acid products which are readily identified but not identical with those in the native peptide.

Mass spectroscopic analyses. A mass spectrum was obtained of HPLC purified material and spectral data were obtained on a Bruker Biflex-III MALDI/TOF mass spectrometer. The instrument was operated in the reflectron mode with an accelerating voltage of 19 KeV. A nitrogen laser (337 nm), with a pulse width of 3 nanoseconds and pulse frequency of 3 Hz was used for desorption and ionization of the sample. The number of spectra obtained on any individual sample varied from 10 to 200 laser shots. The matrix used for co-crystallization of the samples was α-cyano-4-hydroxy cinnamic acid. External calibration for the initial determination of the molecular weights was done with adrenocorticotropic hormone fragment 18-39 (M.W.=2465.2). Fragmentation ion (MS/MS) data on the sample was obtained by application of LC/MS on a Bruker Esquire 3000 system with the sample in acetonitrile having a flow rate of 5 µl/min. The counter current drying gas was at 250° C. having a flow rate of 4.0 l/minute.

Mass spectrometry of coronamycin, on several individual preparations, consistently revealed the presence of a mixture of compounds with the major component having an actual mass of 1203.4 Da followed by another component with an actual mass of 1217.9. It is estimated, by virtue of the signal intensity, that these two major components made up about 80% of the total weight of coronamycin. Three minor components had masses of 1185.8 Da, 1199.8 Da, and 1233.5 Da, respectively, and make up the difference in the total weight of the sample. None of these components appeared to be sodiated. It was also the case that the molecules appeared to be related and differed only with respect to variances in some chemical features in the non-peptide moiety of the compound. For instance, the 1203 Da component differed from the 1217 Da component by a mass of 14 which was most likely accounted for by a methylene—$CH_2$ group. Also, the minor 1199 Da component differed from the 1217 Da component by 18 mass units which was probably a water molecule, and the 1185 Da was 14 mass units different from 1199 Da which was, most likely, another methylene group. The minor 1233 Da component was 16 mass units greater than the 1217 Da component which could be accounted for by an oxygen atom. The structural relatedness of these compounds was also manifested by the concise and consistent amino acid analytical data (Table 1). The LC/MS/MS analysis provided evidence that the molecules of coronamycin were all related by virtue of having the same major fragments after MS/MS of the individual components. As an example, MS/MS of component ions 1217, 1203 and 1233 each yielded common ions at 435, 546, 631, and 960 suggesting the existence of a common core structure.

$^1$H NMR and $^{13}$C NMR spectra. Samples were dissolved in 100% deuterated acetonitrile and data obtained in a Bruker 500 MHz instrument. In $^1$H spectroscopy, each sample was subjected to 16 scans with a sweep width of 6024 and 8 k real points.

The $^1$H NMR spectrum of coronamycin as shown in FIG. 4 resembled that of a peptidyl-like compound (Ballio et al., 1994, supra; Strobel et al., 1999, supra). In addition, the signals at 7.6-7.7 ppm could be accounted for by the resonances of the aromatic ring in tyrosine (FIG. 4). The major signal (s) at 1.3 ppm was consistent with multiple methylene carbons as per a fatty acid, (Pouchert and Campbell, 1974, The Aldrich Library of NMR Spectra, Aldrich Chemical Co.). The other signals in the $^1$H spectrum were consistent with shifts commonly associated with peptides (Ballio et al., 1994, supra). Thus, the collective spectral and analytical data supported the conclusion that coronamycin represented a base peptide that was functionalized by one of a number of fatty acid moieties having varying degrees of oxidation, hydration and length of the carbon chain. This conclusion accounted for the presence of each of the components of coronamycin as observed in the mass spectral data and not be too unlike other lipopeptide antibiotics previously observed by us and others (Ballio et al., 1994, supra; Strobel et al., 1999, supra; Miller et al., 1998, supra). Furthermore, it is not uncommon for lipopeptides and other highly functionalized antibiotics to be virtually un-separable as is the case with commercially available echinomycin which also contains a family of related compounds (Waring, 1979, Echinomycin, triosin and related antibiotics, In Antibiotics, vol 5 part 2, Mechanism of Action of Antieukaryotic and Antiviral Compounds. Hahn F. E. ed. p. 173. Springer; Heidelberg; Castillo et al., 2002, Microbiology 148, 2675-2685). Finally, the lipodial nature of coronamycin is worthy of note especially since it contained not only a lipid moiety but also at least 3 residues of leucine. The compound had a strong tendency to adhere to glass surfaces sometimes being responsible for errors in dilution bioassay experiments and may contribute to its relatively poor yields from liquid culture.

Coronamycin appeared to represent a novel group of bioactive substances since a search of the Chapman & Hall Dictionary of Natural Products on CD Rom, 2002 revealed no chemical identity with any previously described natural products. A peptidyl compound, actinomycin $F_1$ has a MW of 1217 Da but does not share any amino acids in common with coronamycin. Likewise antibiotic $A_{41030}$ has a MW of 1233 Da and it also does not share any commonality with coronamycin. The closest chemical relative of coronamycin appeared to be polymyxin $B_1$ whose mass is 1203 Da, a cyclic peptide sharing some resides in common with comamycin such as leucine, and threonine. Actinomycin $D_{11}$ has a mass of 1203 but has no amino acids in common with coronamycin. Interestingly, all other compounds listed in the *Chapman & Hall Dictionary* whose masses are equivalent, or nearly so with coronamycin, each possess one or more sugar residues.

Example 4

Bioassays of Coronamycin Against *Plasmodium falciparum*

An antimalarial assay of coronamycin was performed against *Plasmodium falciparum* according to the procedure of Castillo et al., 2002, *Microbiology* 148, 2675-2685. Cultures of *Plasmodium falciparum* strain CSC-1 (Honduras) were maintained according to the methods of Trager and Jensen, 1976, *Science* 193: 673-675; and Trager and Jensen, 1978, *Nature* 273: 621-622, except that human serum was replaced with Albumax I (Gibco, BRL); 6% w/v stock solution in RPMI 1640 medium (Trager and Jensen, 1976, supra; Trager and Jensen, 1978, supra) containing 0.1 mg $ml^{-1}$ hypoxanthine stored at −20° C. All cultures were maintained in a microaerophilic environment containing 1% oxygen/5% $CO_2$ with the balance being nitrogen. The stock solution was diluted at a ratio of 1:20 v/v of RPMI 1640 to give a final concentration of 0.3% Albumax I. Stock solutions of the compounds to be tested, including choloroquine, were initially dissolved in DMSO or water and diluted to final concentrations in Albumax-supplemented RPMI 1640 medium. Control cultures contained the same quantity of DMSO or water as that used in the experimental trials. Data were reported as $IC_{50}$ values.

Parasite cultures, adjusted to 0.1-0.5% parasitemia by addition of freshly washed human erythrocytes, were pipetted into 96 well culture plates by adding 10 μl of a 50% cell suspension to each well to give a final volume of 5 μl of packed erythrocytes per well. The test compounds in RPMI 1640 were added at 95 μl per well to four wells per each concentration of test compound. Quadruplicate control wells were treated similarly with DMSO or water added without the test compounds present. The cultures were gassed and exposed to radiolabeled $^3$[H]-phenylalanine (1 microcurie per well) for the final 24 hour of treatment. Cultures were monitored for bacterial contamination and for parasite viability by Giemsa staining of thin films. Ultimately, the cells were harvested onto glass-fiber filters, followed by liquid scintillation counting. The $IC_{50}$ for each compound was determined by linear regression analysis using 50% of the control counts as the regression point. The experiment was repeated three times, the data averaged, and the standard deviation of the mean determined. The $IC_{50}$ of coronamycin was defined as the concentration of compound which yielded 50% viability.

Coronamycin showed strong activity against *Plasmodium falciparum,* the most pathogenic agent of malaria. The $IC_{50}$ values were 9±7.3 ng $ml^{-1}$. The low $IC_{50}$ values of coronamycin were in the same range as chloroquine, the gold standard antimalarial compound, which has an $IC_{50}$ at 7.0 ng $ml^{-1}$.

Example 5

Bioassays of Coronamycin Against Pythiaceous Organisms

Coronamycin was bioassayed against *Pythium ultimum* using the procedure described in Example 2. Coronamycin was especially active against *Pythium ultimum* with an MIC value of 2 μg $ml^{-1}$.

Example 6

Bioassays of Coronamycin Against Bacteria and Fungi

Coronamycin was tested by disk diffusion at 20 μg per disk against a representative panel of human pathogenic bacteria according to a protocol previously described (Castillo et al., 2002, supra). This panel included *Pseudomonas aeruginosa* (ATCC 27853), *Klebsiella pneumoniae* (ATCC 10031), *Enterococcus faecium* (ATCC 49624), *Staphylococcus aureus* (ATCC 29213), *Enterococcus faecalis* VRE (ATCC 51299) and *Streptococcus pneumoniae* (ATCC 10031). Inhibition was observed only against *Streptococcus pneumoniae* with a 7 mm zone of inhibition. No further anti-bacterial assays of coronamycin were pursued.

In comparable disk diffusion assay tests, coronamycin was tested against several plant pathogenic fungi. Growth was monitored over time and the MIC was determined after 48 hours at 23° C. as the lowest concentration of coronamycin producing no growth of the test fungus.

The results shown in Table 2 indicated that coronamycin had activity against *Phytophthora* and *Aphanomyces,* but had little activity against other plant pathogenic fungi.

TABLE 2

MIC values against plant pathogenic fungi

| Test fungus | MIC (μg × $ml^{-1}$) |
|---|---|
| *Phytophthora cinnamomi* | 16.0 |
| *Aphanomyces cochliodiodes* | 4.0 |
| *Geotrichum candidum* | >500 |
| *Aspergillus fumigatus* | >500 |
| *Aspergillus ochraceus* | >500 |
| *Fusarium solanii* | >500 |
| *Rhizoctonia solani* | >500 |

Microbroth dilution assays of human pathogenic yeasts were performed as described in the NCCLS M27A (NCCLS, 1997) with the addition of Alamar Blue (Trek Diagnostics Systems, Inc., Westlake, Ohio) as a colorimetric indicator of viability (Espinel-Ingroff et al., 1999, *J. Clin. Microbiol.* 37: 591-595). All isolates were obtained from the ATCC. The assays were performed in sterile 96 well plates. The total volume per well was 100 μl. Two wells were inoculated for a given concentration. The MIC was defined as that concentration of compound resulting in no visible growth of the test organism after 24 to 48 hours of incubation with the exception of *Cryptococcus neoformans* which was read at 72 hours. Flucytosine was included as a control antifungal compound.

The results shown in Table 3 demonstrated that the most sensitive human pathogenic yeast to coronamycin was *C. neoformans* which had an MIC of 4.0 μg $ml^{-1}$ at 72 hours (Table 3). However, the MIC was 0.065 μg $ml^{-1}$ at 48 hours for *C. neoformans.* It is apparent that this organism was sensitive to coronamycin while most of the other yeasts tested have MICs greater than 16 μg $ml^{-1}$ (Table 3). Flucytosine was used as a control and the MICs obtained were within the expected range.

TABLE 3

MIC determination of coronamycin against a number of yeasts.

| Organism (ATCC #) | Coronamycin MIC μ$ml^{-1}$ | Flucytosine MIC μ$ml^{-1}$ |
|---|---|---|
| *Cryptococcus neoformans* (ATCC 32045) | 4 | 8 |
| *Candida parapsilosis* (ATCC 90018) | >32 | 0.12 |

TABLE 3-continued

MIC determination of coronamycin against a number of yeasts.

| Organism (ATCC #) | Coronamycin MIC µml$^{-1}$ | Flucytosine MIC µml$^{-1}$ |
|---|---|---|
| Candida albicans (ATCC 90028) | 16-32 | 0.5 |
| Saccharomyces cerevisiae (ATCC 9763) | >32 | <=0.06 |
| Candida parapsilosis (ATCC 22019) | >32 | 0.5 |
| Candida albicans (ATCC 24433) | >32 | 1.0 |
| Candida krusei (ATCC 6258) | >32 | 16 |
| Candida tropicalis (ATCC 750) | >32 | <=0.06 |

Example 7

Anticancer Cell Line Tests for Coronamycin

Coronamycin was tested against human cancer cell line BT20 (breast epithelial cancer, ATCC) and human primary mammary epithelial cells (HMECs) (Clonetics; Biowhittaker, Walkersville, Md.) using a CellTiter 96® Aqueous Non-Radioactive Cell Proliferation Assay kit from Promega (Madison, Wis.). The BT20 cells were grown in the medium recommended by ATCC and were seeded into 96 well clear flat bottom plates at 3000 cells per well in 100 µl. The primary mammary cells were cultured as recommended by the manufacturer in mammary epithelial cell growth media (MEGM®) and were seeded at 3200 cells per well in 100 µl.

After seeding, the cells were incubated for five hours at 37° C. before addition of coronamycin. Two-fold serial dilutions of the coronamycin were made in the culture medium, and a volume equal to that of the seeded cells for each dilution was added to the cells. Each plate also contained some wells with cells plus medium only and some wells with medium only as controls. After addition of the compounds, the plates were incubated at 37° C. for 48 hours or 96 hours for the HMEC and BT20 cell lines, respectively. The proliferation assay was performed using the manufacturer's protocols. The IC$_{50}$ of coronamycin was defined as the concentration of compound which gave 50% viability.

The proliferation assay was performed using the manufacturer's protocols; a 20:1 solution of MTS and PMS was mixed and 10 to 40 µl was added to each well depending on the total volume in the wells. The plates were incubated at 37° C. for one to four hours, and the OD$_{490}$ was determined. The OD reading of all wells was corrected for background by subtracting the reading of wells containing medium only. The wells containing cells only were used as a control for 100% viability. The IC$_{50}$ of each compound was defined as the concentration of compound which gave 50% viability and the experiment was repeated three times and the data averaged and the standard deviation of the mean shown.

Cytotoxicity testing of coronamycin against a primary mammary epithelial cell line (HMEC) gave an IC$_{50}$ of 2 µg ml$^{-1}$ whereas, taxol yielded a value of 25-30 µg ml$^{-1}$. In the case of the breast cancer cell line (BT20) coronamycin had an IC$_{50}$ of 1 µg ml$^{-1}$ whereas taxol was 0.009 µg ml$^{-1}$.

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| Streptomyces sp. P-25-2-4 | NRRL 30701 | Jan. 20, 2004 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents substantially pure culture of the deposited strain. The deposit is available as required by foreign patent laws in countries wherein counterparts of the subject application, or its progeny are filed. All restrictions on the public of the material so deposited will be irrevocably removed upon the granting of a patent. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated coronamycin of a *Streptomyces* sp. strain.

2. The isolated coronamycin of claim 1, which comprises a peptide chain comprising component 1, component 2, tyrosine, methionine, and leucine in molar ratios of 2:2:1:1:3, respectively; and has UV absorbances at 208,214, and a broad band at 270 nm with millimolarextinction coefficients of 2.86, 2.03, and 0.23, respectively; HPLC retention time of 36.43 minutes on a Microsorb 100-5 C-18 column, 250×4.6 mm, using 20% acetonitrile:80% water for 90 minutes as an initial elution solvent programmed to a final concentration of 80% acetonitrile at a flow rate of 2 ml/minute; MS/MS component ions of 1203.4, 1217.9, 1185.8, 1199.8, and 1233.5 daltons; a 1H NMR spectrum of FIG. 4.

3. The isolated coronamycin of claim 2, which has biological activity against the parasitic organism, *Plasmodium falciparum*.

4. The isolated coronamycin of claim 2, which has biological activity against the bacterial pathogen, *Streptococcus pneumoniae*.

5. The isolated coronamycin of claim 2, which has biological activity against the fungal pathogen selected from the group consisting of *Pythium ultimum*, *Cryptococcus neoformans*, *Phytophthora cinnamomi*, and *Candida albicans*.

6. The isolated coronamycin of claim 2, which has biological activity against the breast epithelial cancer cell line BT20.

7. The isolated coronamycin of claim 2, which has biological activity against a plant pathogen selected from the group consisting of *Pythium ultimum*, *Phytophthora cinnamomi*, *Cryptococcus neoformans* and *Candida albicans*.

8. The isolated coronamycin of claim 1, which is produced by *Streptomyces* sp NRRL 30701.

* * * * *